(12) United States Patent
Ishida et al.

(10) Patent No.: US 7,576,125 B2
(45) Date of Patent: Aug. 18, 2009

(54) MELANOGENESIS INHIBITOR AND SKIN PREPARATION CONTAINING THE SAME

(75) Inventors: Kenya Ishida, Kanagawa (JP); Eiko Tamai, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 542 days.

(21) Appl. No.: 10/545,006

(22) PCT Filed: Feb. 12, 2004

(86) PCT No.: PCT/JP2004/001496

§ 371 (c)(1),
(2), (4) Date: Aug. 10, 2005

(87) PCT Pub. No.: WO2004/071481

PCT Pub. Date: Aug. 26, 2004

(65) Prior Publication Data

US 2006/0088485 A1   Apr. 27, 2006

(30) Foreign Application Priority Data

Feb. 14, 2003   (JP) .............................. 2003-036311

(51) Int. Cl.
*A61K 31/357*   (2006.01)
(52) U.S. Cl. ...................... 514/464; 549/430
(58) Field of Classification Search ................. 514/464; 549/430
See application file for complete search history.

(56) References Cited

U.S. PATENT DOCUMENTS 3,686,222 A   8/1972   Chodnekar et al. ....... 260/340.5
3,941,884 A *  3/1976   Edwards ..................... 514/464

FOREIGN PATENT DOCUMENTS

| JP | 8-104616 A | 4/1996 |
|----|------------|--------|
| JP | 8-119848 A | 5/1996 |
| JP | 10-29928 A | 2/1998 |
| JP | 2002-29957 A | 1/2002 |

OTHER PUBLICATIONS

Victor, Sandra R. et al., "Toxicity of synthetic piperonyl compounds to leaf-cutting ants and their symbiotic fungus", Database Caplus, XP002282788.

* cited by examiner

*Primary Examiner*—Joseph K. McKane
*Assistant Examiner*—Janet L Coppins
(74) *Attorney, Agent, or Firm*—Kubovcik & Kubovcik

(57) ABSTRACT

A melanogenesis inhibitor characterized by containing at least one kind of piperonyl alcohol represented by the following general formula (1)

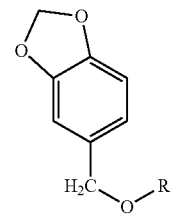

wherein R is a straight chain or branched chain alkyl group having 3 to 18 carbon atoms, a straight chain or branched chain alkenyl group having 3 to 18 carbon atoms, or an optionally substituted alicyclic alkyl group.

The melanogenesis inhibitor is superior in stability and safety and has a high melanogenesis-inhibiting effect; and a skin preparation containing the melanogenesis inhibitor is very stable, safe, and has a sufficient fair skin effect and a sufficient effect for curing skin dyspigmentation.

5 Claims, No Drawings

MELANOGENESIS INHIBITOR AND SKIN PREPARATION CONTAINING THE SAME

This application is a 371 of international application PCT/JP2004/001496, which claims priority based on Japanese patent application No. 2003-036011 filed Feb. 14, 2003, which is incorporated herein by reference.

BACKGROUND OF THE INVENTION

1. Field of the Invention

The present invention relates to a novel melanogenesis inhibitor containing a piperonyl alcohol derivative and a skin preparation containing the novel melanogenesis inhibitor. The present invention further relates to a novel piperonyl alcohol derivative which is included in the above piperonyl alcohol derivative and which is useful as a component of the novel melanogenesis inhibitor.

2. Description of the Prior Art

Chloasmata, Hatchinson's freckles and skin pigmentation increase and become difficult to remove with aging, and are a large worry particularly to persons of middle or advanced age. The mechanism of crisis of these dyspigmentations is still unknown in many respects; however, they are considered to appear because the melanogenesis function at epidermal melanocytes is activated by the action of sunlight (ultraviolet light) or hormones. Inhibition of such melanogenesis or decoloration of generated melanin is a task in development of fair skin preparation or fair skin cosmetic, and various researches have been made.

In fair skin cosmetics for prevention or treatment of chloasmata, Hatchinson's freckles, etc. of skin, there have been compounded L-ascorbic acid and its derivatives, hydroquinone and its derivatives, pyrones (e.g. kojic acid), placenta extract (see, for example, patent literature 3), etc., all of which are well known to have, for example, an effect of melanogenesis inhibition due to hindrance of tyrosinase activity (see, for example, patent literatures 1 and 2) or an effect of decoloration of generated melanin and further have a fair skin effect.

When the above substances are used singly, however, there are various problems. For example, L-ascorbic acid and its derivatives are insufficient in storage stability and do not exhibit the intended effect sufficiently; hydroquinone and its derivatives have a problem in safety (stimulativeness and allergenicity); kojic acid lacks in storage stability (easy to cause coloring); and placenta extract is slow to show its effect. Thus, each substance has been insufficient. Moreover, their effects of melanogenesis inhibition are insufficient. Hence, development of a compound having a higher inhibition effect has been desired.

Patent literature 1: JP-A-10-29928
Patent literature 2: JP-A-8-119848
Patent literature 3: JP-A-8-104616

The present invention aims at providing a melanogenesis inhibitor which is superior in stability and safety, which has a high melanogenesis-inhibiting effect, and which, when made into a skin preparation, is very stable, safe, and has a sufficient fair skin effect and a sufficient effect for curing skin dyspigmentation.

In such a situation, the present inventors made an intensive study on various compounds. As a result, it was found out that the above aim can be achieved by a piperonyl alcohol derivative represented by the following general formula (1)

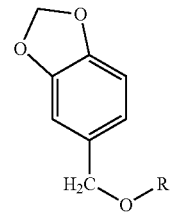

wherein R is a straight chain or branched chain alkyl group having 3 to 18 carbon atoms, a straight chain or branched chain alkenyl group having 3 to 18 carbon atoms, or an optionally substituted alicyclic alkyl group.

That is, the present inventors found out that the piperonyl alcohol derivative represented by the above general formula (1) is superior in stability and safety and has a high melanogenesis-inhibiting effect and that a skin preparation containing the derivative is very stable, safe, and has an excellent fair skin effect and an excellent effect for curing skin dyspigmentation. By a further study, it was made clear that the melanogenesis-inhibiting effect of the present invention compound is expressed not by the tyrosinase activity-hindering effect (possessed by conventional compounds) but by a tyrosinase biosynthesis-hindering effect. The present invention has been completed based on the above finding.

SUMMARY OF THE INVENTION

The present invention includes the following inventions.

(1) A melanogenesis inhibitor characterized by containing at least one kind of piperonyl alcohol represented by the following general formula (1)

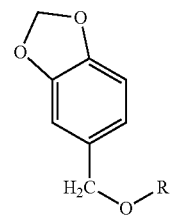

wherein R is a straight chain or branched chain alkyl group having 3 to 18 carbon atoms, a straight chain or branched chain alkenyl group having 3 to 18 carbon atoms, or an optionally substituted alicyclic alkyl group.

(2) A melanogenesis inhibitor according to (1), wherein the R in the general formula (1) is an alicyclic alkyl group derived from a cyclic monoterpene alcohol.

(3) A skin preparation characterized by containing a melanogenesis inhibitor set forth in (1).

(4) A skin preparation characterized by containing 0.001 to 20.0% by mass of a melanogenesis inhibitor set forth in (1).

(5) A skin preparation according to (3) or (4), which has a form of cream, lotion, emulsion, jelly, beauty lotion, pack or ointment.

(6) A piperonyl alcohol derivative characterized by represented by the following general formula (2)

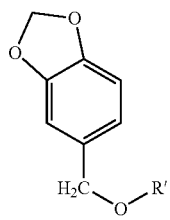

wherein R' is an alicyclic alkyl group derived from a cyclic monoterpene alcohol.

DETAILED DESCRIPTION OF THE INVENTION

The present invention is described in detail below.

In the general formula (1) representing the piperonyl alcohol derivative contained in the melanogenesis inhibitor of the present invention, R is a straight chain or branched chain alkyl group having 3 to 18 carbon atoms, a straight chain or branched chain alkenyl group having 3 to 18 carbon atoms, or an optionally substituted alicyclic alkyl group.

As specific examples of R when R is a straight chain or branched chain alkyl group having 3 to 18 carbon atoms, there can be mentioned straight chain alkyl groups such as n-propyl group, n-butyl group, n-hexyl group, n-octyl group, n-nonyl group, n-decyl group, n-undecyl group, n-dodecyl group, n-tetradecyl group, n-pentadecyl group, hexadecyl group, octadecyl group and the like; and branched chain alkyl groups such as isopropyl group, isobutyl group, sec-butyl group, tert-butyl group, 4-methylpentyl group, 5-methylhexyl group, 2-ethylhexyl group, 6-methylheptyl group, 7-methyloctyl group, 8-methylnonyl group, 2,6 -dimethylheptyl group, 3,7-dimethyloctyl gorup, 3,7,11-trimethyldodecyl group and the like. However, the specific examples are not restricted thereto.

As specific examples of R when R is a straight chain or branched chain alkenyl group having 3 to 18 carbon atoms, there can be mentioned straight chain alkenyl groups such as allyl group, 1-propenyl group, 1-butenyl group, 2-butenyl group, 3-butenyl group, 4-pentenyl group, 5hexenyl group, 6-heptenyl group, 7-octenyl group, 8-nonenyl group, 9-decenyl group, 1-pentenyl group, 1-hexenyl group, 1-heptenyl group, 1-octenyl group, 1-nonenyl group, 1-decenyl group, 9-octadecenyl group and the like; and branched chain alkenyl groups such as isopropenyl group, 2-methyl-1-propenyl group, 3-methyl-2-butenyl group, 4-methyl-3-pentenyl group, 5-methyl-4-hexenyl group, 6-methyl-5-heptenyl group, 7-methyl-6-octenyl group, 8-methyl-7-noneyl group, 1-methyl 1-propenyl group, l-methyl-l-butenyl group, l-methyl-1-pentenyl group, 1-methyl-1-hexenyl group, 1-methyl-l-heptenyl group, 1-methyl-1-octenyl group, 1-methyl-1-nonenyl group, 2,6-dimethyl-5-hetenyl group, 2,6-dimethyl-1-heptenyl group, 3,7-dimethyl-2,6-octadienyl (geranyl, neryl) group, 3,7,11trimethyl-2,6,10-dodecatrienyl (farnesyl) group, 3,7,11trimethyl-6,10-dodecadienyl (dihydrofarnesyl) group and the like. However, the specific examples are not restricted thereto.

As specific examples of R when R is an optionally substituted alicyclic alkyl group, there can be mentioned cyclopentyl group, cyclohexyl group and cycloheptyl group with cyclohexyl group being preferred. However, the specific examples are not restricted thereto.

As specific examples of R when R is an optionally substituted alicyclic alkyl group, there can be mentioned cyclopentyl group, cyclohexyl group and cycloheptyl group with cyclohexyl group being preferred. However, the specific examples are not restricted thereto.

As specific examples of the optionally substituted alicyclic alkyl group, there can be mentioned cyclohexyl group, cyclohexylmethyl group, cyclohexylethyl group, 4-isopropylcyclohexyl group, 4-tert-butylcyclohexyl group, 2,4-dimethyl-3-cyclohexenyl group, 2-tert-butylcyclohexyl group, 4-isopropylcyclohexylmethyl group, 5-methyl-2-(1-methylethenyl) cyclohexyl group (isopulegyl), 5-methyl-2-isopropylcyclohexyl group (p-menthan-3-yl, menthyl), 1-methyl, 4-isopropylcyclohexenyl group (terpinenyl), 1-methyl-4-isopropylcyclohexyl group (dihydroterpinenyl), 1-methyl-4-isopropenyl-6-cyclohexen-2-yl group (carvenyl), 6-methyl-3-isopropenylcyclohexenyl group (dihydrocarvenyl), 1-(4-isopropenyl)cyclohexyl)methyl group (perillyl), 4-methyl-1-isopropylbicyclo [3.1.0]hexan-4-yl group (4-thujanyl), 4-methyl-1-isopropylbicyclo[3.1.0]hexan-3-yl group (3-thujanyl), 6,6-dimethylbicyclo[3.1.1]hept-2-en-2-ethyl group (nopyl), 1,3,3-trimethylbicyclo[2.2.1]heptan-2-yl group (fenchonyl) and endo-1,7,7-trimethylbicyclo [2.2.1]heptan-2-yl group (bornyl).

As specific examples of the optionally substituted alicyclic alkyl group, preferred are alicyclic alkyl groups each derived from a cyclic monoterpene alcohol, such as 4-isopropylcyclohexylmethyl gorup, 5-methyl-2-(1-methylethenyl) cyclohexyl group (isopulegyl), 5-methyl-2-isopropylcyclohexyl group (p-menthan-3-yl, menthyl), 1-methyl-4-isopropylcyclohexenyl group (terpinenyl), 1-methyl-4-isopropylcyclohexyl group (dihydroterpinenyl), 1-methyl-4-isopropenyl-6-cyclohexen-2-yl group (carvenyl), 6-methyl-3-isopropenylcyclohexenyl group (dihydrocarvenyl), 1-(4-isopropenyl)cyclohexyl)methyl group (perillyl), 4-methyl-1-isopropylbicyclo[3.1.0]hexan-4-yl group (4-thujanyl), 4-methyl-1-isopropylbicyclo[3.1.0]hexan-3-yl group (3-thujanyl), 6,6-dimethylbicyclo[3.1.1]hept-2-en-2-ethyl group (nopyl), 1,3,3-trimethylbicyclo[2.2.1]heptan-2-yl group (fenchonyl) and endo-1,7,7-trimethylbicyclo[2.2.1]heptan-2-yl group (bornyl). Particularly preferred is 5-methyl-2-isopropylcyclohexyl (p-menthan-3-yl, menthyl) group from the standpoint of safety, solubility and effect of the piperonyl alcohol derivative represented by the general formula (1).

Therefore, as specific examples of the piperonyl alcohol represented by the general formula (1), there can be mentioned, when R of the general formula (1) is a straight chain or branched chain alkyl group having 3 to 18 carbon atoms or a straight chain or branched chain alkenyl group having 3 to 18 carbon atoms, 3,4-methylenedioxybenzyl n-propyl ether (piperonyl n-propyl ether), 3,4-methylenedioxybenzyl n-butyl ether (piperonyl n-butyl ether), 3,4-methylenedioxybenzyl n-hexyl ether (piperonyl n-hexyl ether), 3,4-methylenedioxybenzyl 2-ethylhexyl ether (piperonyl 2-ethylhexyl ether), 3,4-methylenedioxybenzyl 3,7-dimethyl-2,6-octadienyl ether (piperonyl geranyl ether), 3,4-methylenedioxybenzyl 3,7,11-trimethyl-2,6,10-dodecatrienyl ether (piperonyl farnesyl ether); and when R is an alicyclic alkyl group, 3,4-methylenedioxybenyl cyclohexyl ether (piperonyl cyclohexyl ether), 3,4-methylenedioxybenzyl 5-methyl-2-(1-methylethenyl)cyclohexyl ether (piperonyl isopulegyl ether), 3,4-methylenedioxybenzyl 5-methyl-2-isopropylcyclohexyl ether (piperonyl menthyl ether), 3,4-methylenedioxybenzyl 1-methyl-4-isopropylcyclohexenyl ether (piperonyl terpinenyl ether), 3,4-methylenedioxybenzyl 1-methyl-4-isopropylcyclohexyl ether (piperonyl dihydroterpinenyl ether), 3,4-methylenedioxybenzyl 1-methyl-4-isopropenyl-6ether (piperonyl carvenyl ether), 3,4-cyclohexen-2-yl-methylenedioxybenzyl 6-methyl-3-isopropenylcyclohexyl ether (piperonyl dihydrocarvenylether), 3,4-methylenedioxybenzyl [1-(4-isopropenyl)cyclohexyl]methyl ether (piperonyl perillyl ether), 3,4-methylenedioxybenzyl 4-methyl-1-isopropylbicyclo [3.1.0]hexan-4-yl ether (piperonyl 4-thujanyl ether), 3,4-methylenedioxybenzyl 4-methyl-1-isopropylbicyclo [3.1.0]hexan-3-yl ether (piperonyl 3-thujanyl ether), 3,4-methylenedioxybenzyl 6,6-dimethylbicyclo [3.1.1]hept-2-en-2-ethyl ether (piperonyl nopyl ether), 3,4-methylenedioxybenzyl 1,3,3-trimethylbicyclo [2.2.1]heptan-2-yl ether (piperonyl fenchonyl ether) and 3,4-methylenedioxybenzyl endo-1,7,7-trimethylbicyclo [2.2.1]heptan-2-yl ether (piperonyl bornyl ether).

Of the piperonyl alcohol derivatives represented by the general formula (1), contained in the melanogenesis inhibitor of the present invention, a piperonyl alcohol derivative represented by the general formula (2) wherein R' is an alicyclic alkyl group derived from a cyclic monoterpene alcohol, i.e. a residue obtained by removing a hydroxyl group from a cyclic monoterpene alcohol, is a novel compound hitherto unknown, shows a striking melanogenesis-inhibiting property, and is safe and storable.

As specific examples of the piperonyl alcohol derivative represented by the general formula (2), there can be mentioned 3,4-methylenedioxybenzyl 5-methyl-2-(1cyclohexyl ether (piperonyl isopulegyl ether), -methylethenyl) 3,4-methylenedioxybenzyl 5-methyl-2-isopropylcyclohexyl ether (piperonyl menthyl ether), 3,4-methylenedioxybenzyl 1-methyl-4-isopropylcyclohexenyl ether (piperonyl terpinenyl ether), 3,4-methylenedioxybenzyl 1-methyl-4-isopropylcyclohexyl ether (piperonyl dihydroterpinenyl ether), 3,4-methylenedioxybenzyl 1-methyl-4-isopropenyl-6-cyclohexen-2-yl ether (piperonyl carvenyl ether), 3,4-methylenedioxybenzyl 6-methyl-3-isopropenylcyclohexenyl ether (piperonyl dihydrocarvenyl ether), 3,4-methylenedioxybenzyl [1-(4-isopropenyl)cyclohexyl]methyl ether (piperonyl perillyl ether), 3,4-methylenedioxybenzyl 4-methyl-1-isopropylbicyclo[3.1.0]hexan-4-yl ether (piperonyl 4-thujanyl ether), 3,4-methylenedioxybenzyl 4-methyl-1-isopropylbicyclo [3.1.0]hexan-3-yl ether (piperonyl 3-thujanyl ether), 3,4-methylenedioxybenzyl 6,6-dimethylbicyclo [3.1.1]hept-2-en-2-ethyl ether (piperonyl nopyl ether), 3,4-methylenedioxybenzyl 1,3,3-trimethylbicyclo[2.2.1]heptan-2-yl ether (piperonyl fenchonyl ether) and 3,4-methylenedioxybenzyl endo-1,7,7-trimethylbicyclo [2.2.1]heptan-2-yl ether (piperonyl norbonyl ether). In particular, 3,4-methylenedioxybenzyl 5-5-methyl-2-isopropylcyclohexyl ether (piperonyl menthyl ether) is preferred.

Each compound of the present invention represented by the general formula (1) or (2) can be synthesized by, for example, the following method. That is, the compound can be produced, for example, by reducing 3,4-methylenedioxybenzaldehyde (heliotropin) (easily obtainable as a commercial product) using hydrogen catalytically in the presence of a noble metal (e.g. Raney nickel) catalyst or using a metal hydride (e.g. sodium boron hydride) to convert it into 3,4-methylenedioxybenzyl alcohol, reacting the alcohol with a hydrogen halide to convert it into a 3,4-methylenedioxybenzyl halide, and then reacting the halide with an alkoxide (produced from a hydroxy hydrocarbon) in the presence of a base, or converting the 3,4-methylenedioxybenzyl alcohol into 3,4-methylenedioxybenzyl alkoxide in the presence of a base and then reacting the alkoxide with a halogenated hydrocarbon group.

The skin preparation of the present invention refers to a preparation applied to pellide (including scalp) as a cosmetic, a drug or a quasi drug. It can be used in various forms such as facial or skin care cosmetic (e.g. cream, lotion, emulsion, pack and fair skin lotion), make-up or body cosmetic (e.g. foundation, lipstick and eye shadow), aromatic cosmetic, scalp and hair cosmetic, wash, jelly, ointment and the like.

The skin preparation of the present invention contains at least one kind selected from the piperonyl alcohol derivatives represented by the general formula (1), i.e. the melanogenesis inhibitors of the present invention. The concentration of the melanogenesis inhibitor can be varied appropriately depending upon the kind of base material, the combination use of other melanogenesis inhibitor, the purpose of application, etc., but ordinarily is preferably 0.001 to 20.0% by mass, more preferably 0.005 to 10.0% by mass relative to the total of the preparation containing the inhibitor. Incidentally, as the other melanogenesis inhibitor, there can be mentioned, for example, L-ascorbic acid and it derivatives, hydroquinone and its derivatives, kojic acid, linoleic acid (ester), lactic acid (ester) and placenta extract.

In the skin preparation of the present invention, there can be used appropriately as necessary, in addition to at least one kind selected from the above-mentioned melanogenesis inhibitors as an essential component, other components ordinarily used in skin preparations (e.g. cosmetics and drugs), such as powder component, oil and fat, wax, hydrocarbon oil, higher fatty acid, higher alcohol, synthetic ester oil, silicone, anionic surfactant, cationic surfactant, amphoteric surfactant, nonionic surfactant, humectant, water-soluble high-molecular compound, thickening agent, film-making agent, ultraviolet absorber, sequestering agent, lower alcohol, polyhydric alcohol, saccharide, amino acid derivative, organic amine, synthetic resin emulsion, pH-adjusting agent, skin nutrient, vitamin, anti-oxidant, anti-oxidizing aid, perfume and water.

Specific examples of usable components are listed below. The skin preparation of the present invention can be produced by compounding at least one kind selected from these components together with the above-mentioned essential component and employing an ordinary method.

As the powder component, there can be mentioned, for example, inorganic white pigments such as talc, kaolin, mica, magnesium carbonate, calcium carbonate, aluminum silicate, barium silicate, calcium silicate, magnesium silicate, strontium silicate, metal tungstate, magnesium, silica, zeolite, barium sulfate, calcined calcium sulfate (calcined gypsum), calcium phosphate, hydroxyapatite, ceramic powder, metal soap (zinc myristate, calcium palmitate, aluminum stearate), polyamide resin powder (nylon powder), polyethylene powder, polymethyl methacrylate powder, polystyrene powder, styrene/acrylic acid copolymer resin powder, organic powder (e.g. cellulose powder), titanium dioxide, zinc oxide and the like; inorganic red pigments such as iron oxide (red iron oxide), iron titanate and the like; inorganic violet pigments such as carbon black, Congo Violet, cobalt violet and the like; inorganic green pigments such as cobalt titanate and the like; inorganic blue pigments such as ultramarine, prussian blue and the like; pearl pigments such as titanium oxide-coated mica, titanium oxide-coated bismuth oxychloride, titanium oxide-coated talc, colored titanium oxide-coated mica, bismuth oxychloride, fish scale leaves and the like; metal powder pigments such as aluminum powder, copper powder and the like; organic pigments such as Red 201, Red 202, Red 204, Red 205, Red 220, Red 226, Red 228, Red 405, Orange 203, Orange 204, Yellow 205, Yellow 401, Blue 404 and the like; organic pigments of, for example, zirconium, barium or aluminum lake, such as Red 3, Red 104, Red 106, Red 227, Red 230, Red 401, Red 505, Orange 205, yellow 4, Yellow 5, Yellow 202, Yellow 203, Green 3, Blue 1 and the like; and natural coloring matter such as chlorophyll, β-carotene and the like. The powder component may be any as long as it is applicable to ordinary cosmetics. It is not restricted to those mentioned above.

As the liquid oil and fat, there can be mentioned, for example, avocado oil, tsubaki oil, turtle oil, macadamia nut oil, corn oil, mink oil, olive oil, rape seed oil, yolk oil, sesame oil, wheat germ oil, castor oil, linseed oil, safflower oil, cotton seed oil, soybean oil, peanut oil, tea seed oil, rice bran oil, jojoba oil, germ oil, triglycerine, trioctanoic acid glyceride and triisopalmitic acid glyceride.

As the solid oil and fat, there can be mentioned, for example, cacao fat, coconut oil, horse oil, hardened coconut oil, palm oil, beef tallow, sheep fat, hardened beef tallow, palm kernel oil, lard, beef bone fat, Japan wax kernel oil, hardened oil, beef foot oil, Japan wax and hardened castor oil.

As the wax, there can be mentioned, for example, bees wax, candelilla wax, cotton wax, carnauba wax, bayberry wax, insect wax, spermaceti, lanolin, lanolin acetate, liquid lanolin, isopropyl ester of lanolin fatty acid, hexyl laurate, reduced lanolin, jojoba wax, hard lanolin, POE (polyoxyethylene) lanolin alcohol ether, POE lanolin alcohol acetate, POE cholesterol ether, polyethylene glycol ester of lanolin fatty acid and POE hydrogenated lanolin alcohol ether.

As the hydrocarbon oil, there can be mentioned, for example, liquid paraffin, squalene, paraffin and vaseline.

As the higher fatty acid, there can be mentioned, for example, lauric acid, myristic acid, palmitic acid, stearic acid, oleic acid, 1,2-hydroxystearic acid, undecylenic acid, tall oil, isostearic acid, linolic acid, linolenic acid, eicosapentaenoic acid (EPA) and docosahexaenoic acid (DHA).

As the higher alcohol, there can be mentioned, for example, straight chain alcohols such as lauryl alcohol, cetyl alcohol, stearyl alcohol, behenyl alcohol, myristyl alcohol, oleyl alcohol, cetostearyl alcohol and the like; and branched chain alcohols such as monostearyl glycerine ether, 2-decyltetradecynol, lanolin alcohol, cholesterol, phytosterol, hexyldodecanol, isostearyl alcohol, octyldodecanol and the like.

As the synthetic ester oil, there can be mentioned, for example, isopropyl myristate, cetyl octanoate, octyl dodecyl myristate, isopropyl palmitate, butyl stearate, hexyl laurate, myristyl myristate, decyl oleate, hexyl dodecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol-fatty acid ester, neopentyl glycol dicaprate, diisostearyl malate, glycerine di-2-heptylundecanoate, trimethylolpropane tri-2-ethylhexylate, trimethylolpropane triisostearate, pentaerythritol tetra-2-ethylhexylate, glycerine tri-2-ethylhexylate, trimethylolpropane triisostearate, cetyl 2-ethylhexanoate, 2-ethylhexyl palmitate, glycerine trimyristate, tri-2-heptylundecanoic acid glyceride, methyl ester of castor oil fatty acid, oleic acid oil, setostearyl alcohol, 2-heptylundecyl palmitate, diisobutyl adipate, 2-octyldodecyl N-layroyl-L-glutamate, di-2-heptylundecyl adipate, ethyl laurate, 2-hexyldecyl myristate, 2-hexyldecyl palmitate, 2-heyldecyl adipate, diisopropyl sebacate, 2-ethylhexyl succinate, ethyl acetate, butyl acetate, amyl acetate and triethyl citrate.

As the silicone, there can be mentioned, for example, chain polysiloxanes such as dimethylpolysiloxane, methylphenylpolysiloxane, methylhydrogenpolysiloxane and the like; alicyclic polysiloxanes such as decamethylpolysiloxane, dodecamethylpolysiloxane, tetramethyltetrahydrogen-polysiloxane and the like; silicone resins having a three-dimensional network; and silicone rubber.

As the anionic surfactant, there can be mentioned, for example, fatty acid soaps such as soap base, sodium laurate, sodium palmitate and the like; salts of higher alkyl sulfates such as sodium lauryl sulfate, potassium lauryl sulfate and the like; salts of alkyl ether sulfates such as triethanolamine POE lauryl sulfate, sodium POE lauryl sulfate and the like; salts of N-acyl sarcosinate such as sodium lauroyl sarcosinate and the like; salts of higher fatty acid amide sulfonates such as sodium N-myristoyl-N-methyltaurinate, sodium coconut oil fatty acid methyl taurate, sodium lauryl methyl taurate and the like; salts of phosphoric acid esters such as sodium POE oleyl ether phosphate, POE stearyl ether phosphate and the like; sulfosuccinic acid salts such as sodium di-2-ethylhexylsulfosuccinate, sodium monolauroylmonoethanol amide polyoxyethylene sulfosuccinate, sodium lauryl polypropylene glycol sulfosuccinate and the like; alkylbenzenesulfonic acid salts such as sodium linear dodecylbenzenesulfonate, triethanolamine linear dodecylbenzenesulfonate, linear dodecylbenzenesulfonic acid and the like; N-acylglutamic acid salts such as monosodium N-lauroylglutamate, disodium N-stearoylglutamate, monosodium N-myristoyl-L-glutamate and the like; salts of higher fatty acid ester sulfates such as sodium hardened cocoyl glyceride sulfate and the like; sulfated oils such as Turkey red oil and the like; POE alkyl ether carboxylates; salts of POE alkyl allyl ether carboxylates; α-olefinsulfonic acid salts; salts of higher fatty acid ester sulfonates; salts of secondary alcohol sulfates; salts of higher fatty acid alkylol amide sulfates; sodium lauroyl monoethanol amide succinate; ditriethanolamine N-palmitoylasparatate; and sodium caseinate.

As the cationic surfactant, there can be mentioned, for example, alkyltrimethylammonium salts such as stearyltrimethylammonium chloride, lauryltrimethylammonium chloride and the like; dialkyldimethylammonium salts such as distearyldimethylammonium chloride and the like; alkylpyridinium salts such as poly(N,N'-dimethyl-3,5-methylenepiperidinium) chloride, cetylpyridinium chloride and the like; alkyl quaternary ammonium salts; alkyldimethylbenzylammonium salts; alkylisoquinolinium salts; dialkylmorpholinium salts; POE alkylamines; alkylamine salts; polyamine fatty acid ester derivatives; amyl alcohol fatty acid ester derivatives; benzalkonium chloride; and benzethonium chloride.

As the amphoteric surfactant, there can be mentioned, for example, imidazoline type amphoteric surfactants such as sodium salt of 2-undecyl-N,N,N-(hydroxyethylcarboxymethyl)-2-imidazoline, disodium salt of 2-cocoyl-2-imidazolinium hydroxide-1-carboxyethyloxy and the like; and betaine type surfactants such as 2-heptadecyl-N-carboxymethyl-N-hydroxyethylimidazolinium betaine, lauryldimethylaminoacetic acid betaine, alkylbetaines, amidobetaine, sulfobetaine and the like.

As the lipophilic nonionic surfactant, there can be mentioned, for example, sorbitan-fatty acid esters such as sorbitan mono-oleate, sorbitan mono-isostearate, sorbitan mono-laurate, sorbitan mono-palmitate, sorbitan mono-stearate, sorbitan sesqui-oleate, sorbitan tri-oleate, di-glycerol sorbitan penta-2-ethylhexylate, di-glycerol sorbitan tetra-2-ethylhexylate and the like; glycerine polyglycerine-fatty acid esters such as mono-cotton seed oil fatty acid glyceride, mono-erucic acid glyceride, sesqui-oleic acid glyceride, mono-stearic acid glyceride, α, α'-oleic acid pyroglutamic acid glyceride, mono-stearic acid malic acid glyceride and the like; propylene glycol-fatty acid esters such as propylene glycol monostearate and the like; hardened castor oil derivatives; and glycerine alkyl ethers.

As the hydrophilic nonionic surfactant, there can be mentioned, for example, POE sorbitan-fatty acid esters such as POE sorbitan mono-oleate, POE sorbitan mono-stearate, POE sorbitan mono-oleate, POE sorbitan tetra-oleate and the like; POE sorbit-fatty acid esters such as POE sorbit mono-laurate, POE sorbit mono-oleate, POE sorbit penta-oleate, POE sorbit mono-stearate and the like; POE glycerine-fatty acid esters such as POE glycerine mono-stearate, POE glycerine mono-isostearate, POE glycerine tri-isostearate and the like; POE-fatty acid esters such as POE mono-oleate, POE di-stearate, POE mono-di-oleate, ethylene glycol di-stearate and the like; POE alkyl ethers such as POE lauryl ether, POE oleyl ether, POE stearyl ether, POE behenyl ether, POE 2-octyldodecyl ether, POE cholestanol ether and the like; POE alkylphenyl ethers such as POE octylphenyl ether, POE nonylphenyl ether, POE di-nonylphenyl ether and the like; bururo nicks such as bururo nick and the like; POE POP alkyl ethers such as POE POP cetyl ether, POE POP 2-decyl tetra-decyl ether, POE POP monobutyl ether, POE POP hydrogenated lanolin, POE POP glycerine ether and the like; tetra-POP tetra-POP ethylenediamine condensates such as tetronics and the like; POE castor oil hardened castor oil derivatives such as POE castor oil, POE hardened castor oil, POE hardened castor oil mono-isostearate, POE hardened castor oil tri-isostearate, POE hardened castor oil mono-pyroglutamic acid mono-isostearic acid diester, POE hardened castor oil maleic acid and the like; POE bees wax lanolin derivatives such as POE sorbit bees wax and the like; alkanol amides such as coconut oil fatty acid diethanol amide, lauric acid mono-ethanol amide, fatty acid isopropanol amide and the like; POE propylene glycol-fatty acid ester; POE alkylamine; POE fatty acid amide; sucrose-fatty acid ester; POE nonylphenyl formaldehyde condensate; alkylethoxydimethylamine oxides; and tri-oleyl phosphate.

As the humectant, there can be mentioned, for example, polyethylene glycol, propylene glycol, glycerine, 1,3-butylene glycol, xylitol, sorbitol, maltitol, chondoroitin sulfate, hyarulonic acid, mucoitin sulfate, cholesteryl 12-hydroxystearate, ceramide, glycosylceramide, sodium lactate, bile acid salt, dl-pyrrolidonecarboxylic acid salt, short chain soluble collagen, di-glycerine (EO) PO adduct, rosa roxburghil extract, extract of *Achillea millefolium* L., melilot extract.

As the natural water-soluble high-molecular compound, there can be mentioned, for example, plant-based high-molecular compounds such as gum arabic, tragacanth gum, galactan, carob gum, karaya gum, carrageenan, pectin, agar, quince seed, algae colloid (brown algae extract), starch (rice, corn, potato, wheat), glycyrrhizic acid and the like; microorganism-based high-molecular compounds such as xanthane gum, dexstran, succinoglucan, pullulan and the like; and animal-based high-molecular compounds such as collagen, casein, albumin, gelatin and the like.

As the semi-synthetic water-soluble high-molecular compound, there can be mentioned, for example, starch type high-molecular compounds such as carboxymethyl starch, methylhydroxypropyl starch and the like; cellulose type high-molecular compounds such as methyl cellulose, nitrocellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose, cellulose powder and the like; and alginic acid type high-molecular compounds such as sodium alginate, alginic acid-propylene glycol ester and the like the synthetic water-soluble high-molecular compound, there can be mentioned, for example, vinyl type high-molecular compounds such as polyvinyl alcohol, polyvinyl methyl ether, polyvinylpyrrolidone, carboxyvinyl polymer (carbopol) and the like; polyoxyethylene type high-molecular compounds such as polyoxyethylene glycol 20,000, 4,000,000 or 600,000 and the like; copolymer type high-molecular compounds such as polyoxyethylene polyoxypropylene copolymer and the like; acrylic type high-molecular compounds such as sodium polyacrylate, polyethyl acrylate, polyacrylamide and the like; polyethyleneimine; and cation polymers.

As the inorganic water-soluble high-molecular compound, there can be mentioned, for example, bentonite, aluminum magnesium silicate (veegum), laponite, hectorite, silicic acid anhydride and the like.

As the thickening agent, there can be mentioned, for example, gum arabic, carrageenan, karaya gum, tragacanth gum, carob gum, quince seed, casein, dextrin, gelatin, sodium pectate, sodium arachate, methyl cellulose, ethyl cellulose, hydroxyethyl cellulose, hydroxypropyl cellulose, sodium polyacrylate, carboxyvinyl polymer, cellulose dialkyldimethylammonium sulfate, xanthane gum, aluminum magnesium silicate and bentonite.

As the ultraviolet absorber, there can be mentioned, for example, benzoic acid type ultraviolet absorbers such as p-aminobenzoic acid (hereinafter abbreviated as PABA), PABA/mono-glycerine ester, N,N-dipropoxyPABA/ethyl ester, N,N-diethoxyPABA/ethyl ester, N,N-dimethylPABA/ethyl ester, N,N-dimethylPABA/butyl ester, N,N-dimethylPABA/octyl ester and the like; anthranilic acid type ultraviolet absorbers such as homomenthyl N-acetylanthranilate and the like; salicylic acid type ultraviolet absorbers such as amyl salicilate, menthyl salicilate, homomenthyl salicilate, octyl salicilate, phenyl salicilate, benzyl salicilate, p-isopropanol phenyl salicilate and the like; cinnamic acid type ultraviolet absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-di-p-methoxycinnamate and the like; benzophenone type ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenylbenzophenone-2-carboxylate, 2-hydroxy-4-n-octoxybenzophenone, 4-hydroxy-3-carboxybenzophenone and the like; 3-(4'-methylbenzylidene)-d,l-camphor; 3-benzilidene-d,l-camphor; urocanic acid; ethyl urocanate; 2-phenyl-5-methylbenzoxazole; 2,2'-hydroxy-5-methylphenyl-benztriazole; 2-(2'-hydroxy-5'-tert-octylphenyl)benztriazole; 2-(2'-hydroxy-5'-methylphenyl)benztriazole; dibenzalazine; dianisoylmethane; 4-methoxy-4'-tert-butyldibenzoylmethane; and 5-(3,3-dimethyl-2-norbornylidene)-3-pentan-2-one.

As the sequestering agent, there can be mentioned, for example, 1-hydroxyethane-1,1-diphosphonic acid, tetra-sodium 1-hydroxyethane-1,1-diphosphonate, di-sodium edetate, tri-sodium edetate, tetra-sodium edetate, sodium citrate, sodium polyphosphate, sodium m-phosphate, gluconic acid, phosphoric acid, citric acid, ascorbic acid, succinic acid and edetic acid.

As the lower alcohol, there can be mentioned, for example, methanol, ethanol, propanol, isopropanol, isobutyl alcohol and tert-butyl alcohol.

As the poly-hydric alcohol, there can be mentioned, for example, di-hydric alcohols such as ethylene glycol, propylene glycol, tri-methylene glycol, 1,2-butylene glycol, 1,3-butylene glycol, tetra-methylene glycol, 2,3-butylene glycol, penta-methylene glycol, 2-butene-1,4-diol, hexylene glycol, octylene glycol and the like; tri-hydric alcohols such as glycerine, trimethylolpropane, 1,2,6-hexanetriol and the like; tetra-hydric alcohols such as pentaerythritol and the like; penta-hydric alcohols such as xylitol and the like; hexa-hydric alcohols such as sorbitol, mannitol and the like; poly-hydric alcohol polymers such as diethylene glycol, dipropylene glycol, triethylene glycol, polypropylene glycol, tetraethylene glycol, diglycerine, polyethylene glycol, triglycerine, tetraglycerine, polyglycerine and the like; di-hydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether and the like; di-hydric alcohol alkyl diethers such as diethylene glycol monomethyl ether, diethylene glycol monoethyl ether, diethylene glycol monobutyl ether, diethylene glycol dimethyl ether, diethylene glycol diethyl ether, diethylene glycol dibutyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether and the like; di-hydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate and the like; glycerine monoalkyl ethers such as chimyl alcohol, selachyl alcohol, batyl alcohol and the like; sugaralcohols such as sorbitol, maltitol, maltotriose, manitol, sucrose, erythritol, glucose, fructose, starch-decomposed sugar, maltose, xylitol, alcohol obtained by reduction of starch-decomposed sugar and the like; grisoride; tetrahydrofurfuryl alcohol; POE tetrahydrofurfuryl alcohol; POP butyl ether; POP POE butyl ether; tripolyoxypropylene glycerine ether; POP glycerine ether; POP glycerine ether phosphate; and POP POE pentaerythritol ether.

As the monosaccharide, there can be mentioned, for example, trioses such as D-glycerylaldehyde, dihydroxyacetone and the like; tetroses such as D-erythrose, D-erythrulose, D-treose, erythritol and the like; pentoses such as L-arabinose, D-xylose, L-lyxose, D-arabinose, D-ribose, D-ribulose, D-xylulose, L-xylulose and the like; hexoses such as D-glucose, D-talose, D-psicose, D-galactose, D-fructose, L-galactose, L-mannose, D-tagatose and the like; heptoses such as aldoheptose, heptulose and the like; octoses such as octulose and the like; deoxysugars such as 2-deoxy-D-ribose, 6-deoxy-L-galactose, 6-deoxy-L-mannose and the like; amino sugars such as D-glucosamine, D-galactosamine, sialic acid, aminouronic acid, muramic acid and the like; uronic acids such as D-glucuronic acid, D-mannuronic acid, L-guluronic acid, D-galacturonic acid, D-iduronic acid and the like.

As the oligosaccharide, there can be mentioned, for example, sucrose, gentianose, umbelliferose, lactose, planteose, iso-maltose, α, α-trehalose, raffinose, maltose, sorbitol, stachose and verbascose.

As the polysaccharide, there can be mentioned, for example, cellulose, quince seed, chondroitin sulfate, starch, galactan, starch sulfate, glycogen, gum arabic, heparan sulfate, hyaluronic acid, tragacanth gum, chondroitin, xanthane gum, mucoitin sulfate, guar gum, dexstran and caronic acid.

As the amino acid, there can be mentioned, for example, neutral amino acids such as glycine, alanine, valine, leucine, isoleucine, serine, threonine, tryptophane, cystine, systeine, methionine, proline, hydroxyproline and the like; acidic amino acids such as aspartic acid, glutamic acid, asparagine, glutamine and the like; and basic amino acids such as alginine, histidine, lysine, hydroxylysine and the like:

As the amino acid derivative, there can be mentioned, for example, sodium acylsarcosinate (sodium lauroylsarcosinate), acylglutamic acid salt, sodium acyl-β-alaninate, glutathione and pyrrolidonecarboxylic acid.

As the organic amine, there can be mentioned, for example, monoethanolamine, diethanolamine, triethanolamine, morpholine, triisopropanolamine, 2-amino-2-methyl-1,3-propanediol and 2-amino-2-methyl-1-propanol.

As the synthetic resin emulsion, there can be mentioned, for example, acrylic resin emulsion, polyethyl acrylate emulsion, acrylic resin solution, polyalkyl acrylate emulsion and polyvinyl acetate resin emulsion.

As the pH-adjusting agent, there can be mentioned, for example, buffer solutions such as lactic acid-sodium lactate, citric acid-sodium citrate and the like.

As the vitamin, there can be mentioned, for example, vitamins A, B1, B2, B6 and E and their derivatives; pantothenic acid and its derivatives; and biotin.

As the anti-oxidant, there can be mentioned, for example, tocopherols, dibutylhydroxytoluene, butylhydroxyanisole and gallic acid esters.

As the anti-oxidizing aid, there can be mentioned, for example, phosphoric acid, citric acid, ascorbic acid, maleic acid, malonic acid, succinic acid, fumaric acid, cephalin, hexametaphosphate, phytic acid and ethylenediaminetetraacetic acid.

The skin preparation of the present invention can be made in various forms such as solution, soluble form, emulsion, oil solution, gel, powder, water/oil two layers, water-oil-powder three layers and the like. The essential component of the present invention is compounded with at least one kind selected from the above-mentioned components, and the compound can be made into a form suitable for intended application, by an ordinary method.

The present invention is described in detail below by way of Examples. However, the present invention is in no way restricted to these Examples.

The measuring apparatuses and measuring conditions used in the Examples are shown below.

(1) Gas Chromatograph (G.C.)

Apparatus: HP-5890A (produced by Hewlett Packard Co.)

Column: Neutrabond-1 (25 m×0.25 m) (produced by GL Sciences Inc.)

Carrier gas: helium

Measurement temperature: 100 to 220° C. (temp. elevation rate: 4° C./min)

(2) Proton NMR Spectrum ($^1$H-NMR)

Apparatus: AM-400 (400 MHz) (produced by Bruker Corporation)

Internal standard substance: tetramethylsilane (3) Mass Spectrum (MS)

Apparatus: M-80B mass spectrometer (ionization voltage: 20 eV) (produced by Hitachi, Ltd.)

First, in-depth description is made on synthesis examples of the piperonyl alcohol derivative of the present invention.

SYNTHESIS EXAMPLE 1

Synthesis of Piperonyl Alcohol

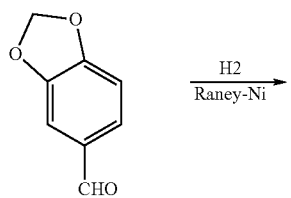

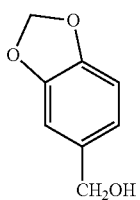

In a 500-ml autoclave were placed 90 g (0.60 mol) of heliotropin, 270 ml of 1-propanol and 3 g of a Raney nickel catalyst (Raney-Ni). Hydrogen gas was filled therein up to 4 MPa. The autoclave contents were stirred at 90° C. for about 10 hours. The reaction mixture was filtered and the filtrate was concentrated. The resulting residue was purified by silica gel column chromatography (hexane:ethyl acetate=20:1) to obtain 27.6 g of piperonyl alcohol as white crystals (yield: 30.3%, G.C. purity: 98.4%)

m.p.: 49-51° C.

$^1$H-NMR (CDCl$_3$, δ ppm): 1.86 (s,1H), 4.56 (s,2H), 5.95 (s,2H), 6.77-6.79 (m,2H), 6.85 (s,1H)

MS: 152 (M$^+$), 135, 123, 105, 93, 77, 65, 51, 39, 29

SYNTHESIS EXAMPLE 2

Synthesis of piperonyl n-butyl ether

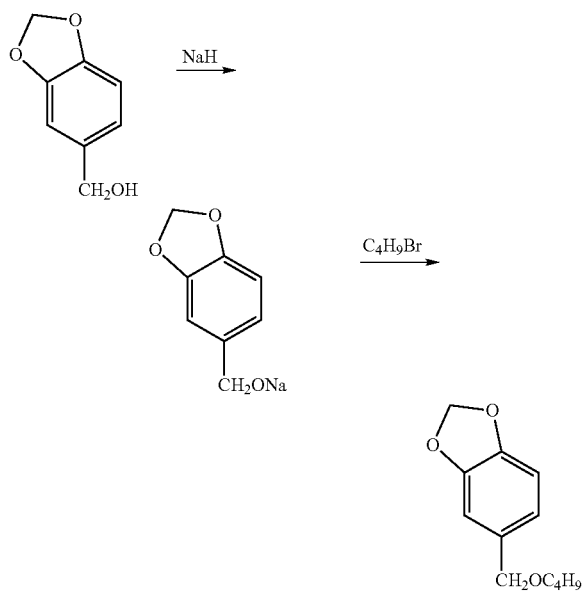

4 g of sodium hydride (60%) and 100 ml of tetrahydrofuran (THF) were stirred in a nitrogen stream. Thereto was dropwise added, in 30 minutes, 15.2 g (0.1 mol) of piperonyl alcohol dissolved in 70 ml of THF, followed by stirring for 30 minutes. Thereto was dropwise added 13.7 g (0.1 mol) of 1-bromobutane dissolved in THF, followed by stirring for 12 hours. The stirring was stopped and the reaction mixture was concentrated. The concentrate was dropped into an excess amount of a 2 N aqueous hydrochloric acid solution. Heptane was added thereto for extraction. The extract was washed with water until the washings became neutral, and then concentrated. The concentrate was purified by silica gel column chromatography (hexane:ethyl acetate=30:1) to obtain 8.0 g of piperonyl butyl ether at a yield of 38.5% as a transparent oily substance.

$^1$H-NMR (CDCl$_3$, δ ppm): 0.91 (t,J=7.5 Hz,3H), 1.39 (m,2H), 1.59 (m,2H), 3.44 (t,J=5.6 Hz, 2H), 4.39 (s,2H), 5.94 (s,2H), 6.77-6.79 (m,2H), 6.85 (s,1H)

MS: 208 (M$^+$), 151, 135, 123, 106, 93, 77, 65, 51, 41, 29

SYNTHESIS EXAMPLES 3 TO 9

Piperonyl alkyl ether compounds shown in Table 1, each having a different hydrocarbon group R in the general formula (1) were produced in the same manner as in Synthesis Examples 1 and 2. The G.C. purities of the individual compounds were as follows.

TABLE 1

| Synthesis Example | R (hydrocarbon group) | G.C. purity |
| --- | --- | --- |
| 3 | Methyl | 99.8% |
| 4 | Ethyl | 99.7% |
| 5 | Propyl | 99.8% |
| 6 | Isobutyl | 97.2% |
| 7 | Isoamyl | 98.3% |
| 8 | Hexyl | 99.7% |
| 9 | Octyl | 99.8% |

The analytical data of the compounds shown in Table 1 are given below.

Piperonyl methyl ether C$_9$H$_{10}$O$_3$ $^1$H-NMR (CDCl$_3$, δ ppm): 3.34 (s,3H), 4.34 (s,2H), 5.93 (s,2H), 6.77 (t,2H), 6.83 (s,1H)

MS: 166 (M$^+$), 150, 135, 121, 105, 93, 77, 65, 51, 28

Piperonyl ethyl ether C$_{10}$H$_{12}$O$_3$ $^1$H-NMR (CDCl$_3$, δ ppm): 1.23 (t,3H), 3.52 (m,2H), 4.40 (s,2H), 5.94 (s,2H), 6.78 (m,2H), 6.86 (d,1H)

MS: 180 (M$^+$), 151, 135, 123, 106, 93, 77, 65

Piperonyl n-propyl ether C$_{11}$H$_{14}$O$_3$ $^1$H-NMR (CDCl$_3$, 6 ppm): 0.93 (t,3H), 1.61 (m,2H), 3.40 (t,2H), 4.40 (s,2H), 5.93 (s,2H), 6.77 (m,2H), 6.85 (m,1H)

MS: 194 (M$^+$), 151, 135, 123, 106, 93, 77

Piperonyl isobutyl ether C$_{12}$H$_{16}$O$_3$ $^1$H-NMR (CDCl$_3$, δ ppm): 0.92 (d,6H), 1.89 (m,1H), 3.20 (d,2H), 4.39 (s,2H), 5.94 (s,2H), 6.78 (m,2H), 6.85 (d,1H)

MS: 208 (M$^+$), 151, 135, 123, 106, 77

Piperonyl isoamyl ether C$_{13}$H$_{18}$O$_3$ $^1$H-NMR (CDCl$_3$, δ ppm): 0.89 (m,6H), 1.51 (m,2H), 1.65 (m,1H), 3.46 (t,2H), 4.38 (s,2H), 5.94 (s,2H), 6.78 (m,2H), 6.84 (s,1H)

MS: 222 (M$^+$), 151, 135, 123, 106, 93, 77, 43

Piperonyl n-hexyl ether C$_{14}$H$_{20}$O$_3$ $^1$H-NMR (CDCl$_3$, δ ppm): 0.89 (t,3H), 1.30 (m,6H), 1.61 (m,2H), 3.43 (t,2H), 4.38 (s,2H), 5.94 (s,2H), 6.78 (m,2H), 6.85 (t,1H)

MS: 236 (M$^+$), 151, 135, 123, 106, 93, 77, 43

Piperonyl n-octyl ether C$_{16}$H$_{24}$O$_3$ $^1$H-NMR (CDCl$_3$, δ ppm): 0.88 (t,3H), 1.29 (m,10H), 1.58 (m,2H), 3.43 (t,2H), 4.39 (s,2H), 5.93 (s,2H), 6.77 (m,2H), 6.85 (d,1H)

MS: 264 (M$^+$), 151, 136, 123, 106, 93, 77, 57, 43

SYNTHESIS EXAMPLE 10

Synthesis of piperonyl l-menthyl ether

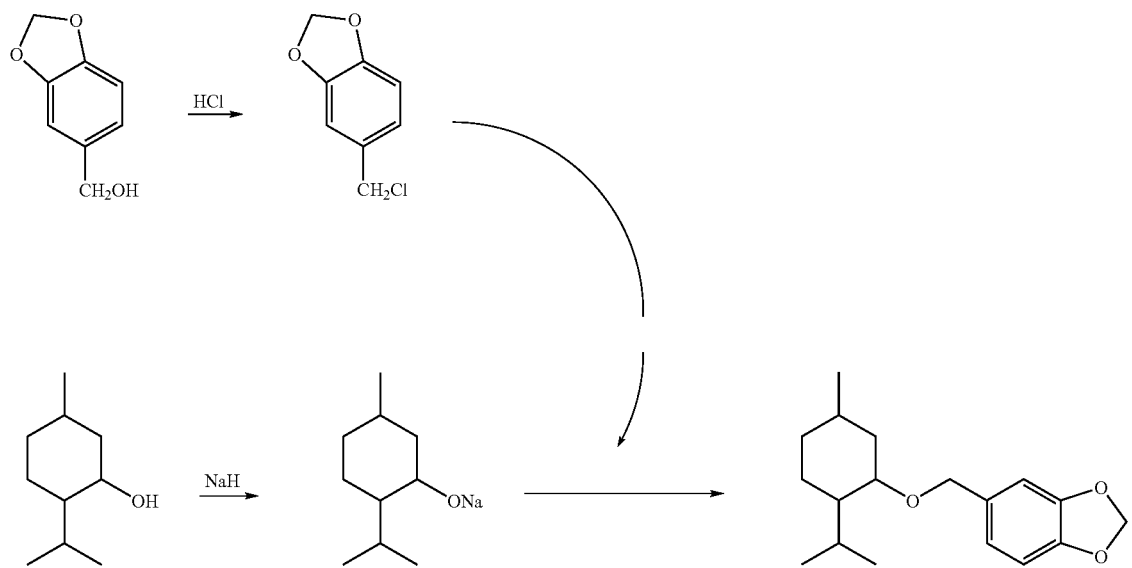

In a 500-ml flask were placed 30 g (0.2 mol) of piperonyl alcohol, 102.8 g (1.0 mol) of a 35% aqueous hydrochloric acid solution and 150 ml of toluene. They were stirred in a nitrogen stream at 90° C. for about 2 hours. The stirring was stopped and phase separation was made to remove the aqueous phase. The toluene phase was washed with water and an aqueous $NaHCO_3$ solution in this order, and then with water several times. The toluene phase was concentrated under reduced pressure to obtain 32.28 g of piperonyl chloride. In a 500-ml flask were placed 8.4 g (0.21 mol) of sodium hydride and 100 ml of toluene, and they were stirred under refluxing in a nitrogen stream, in a 120° C. oil bath. Thereto was dropwise added, in 20 minutes, 29.6 g (0.19 mol) of l-menthol dissolved in 30 ml of toluene. 30 minutes later, 32.3 g (0.19 mol) of the piperonyl chloride dissolved in 32 ml of toluene was added dropwise, followed by stirring for about 1 hour. The stirring was stopped and 110 ml of a 2 N aqueous hydrochloric acid solution was added to terminate a reaction, after which phase separation was made. The toluene phase was washed with water three times and then concentrated. The resulting concentrate was distilled for purification to obtain 35.6 g (yield: 30.6%, purity: 97.2%) of piperonyl l-mentyl ether as a transparent oily substance.

b.p.: 169° C./200 Pa $^1$H-NMR ($CDCl_3$, δ ppm): 0.72 (d,3H), 0.89 (m,9H), 1.27 (m,2H), 1.64 (m,2H), 2.17 (m,1H), 2.28 (m,1H), 3.15 (m,1H), 4.31 (d,1H), 4.53 (d,1H), 5.93 (s,2H), 6.78 (m,2H), 6.85 (s,1H)

COMPARATIVE SYNTHESIS EXAMPLE 1

Synthesis of vanillyl ethers

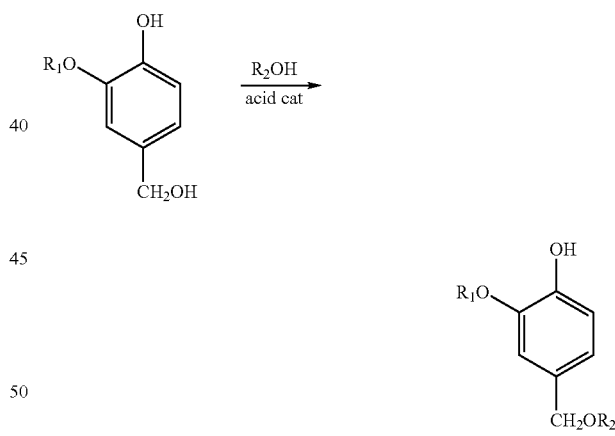

Various vanillyl alcohols were produced in the same manner as in Synthesis Example 1 except that vanillin (X=OH, Y=OMe) or ethylvanillin (X=OH, Y=OEt) was used in place of the heliotropin used in Synthesis Example 1. Using these vanillyl alcohols, vanillyl ethers having different substituents $R_1$ were produced according to the method described in JP-A-57-9729. Also, 3,4-dimethoxybenzyl alcohol was produced in the same manner as in Synthesis Example 1 except that methylvanillin (X=Y=OMe) was used in place of the heliotropin used in Synthesis Example 1. Using this alcohol, vanillyl ethers having different substituents $R_1$ were produced in the same manner as in Synthesis Example 10.

COMPARATIVE SYNTHESIS EXAMPLE 2

Synthesis of piperonyl esters

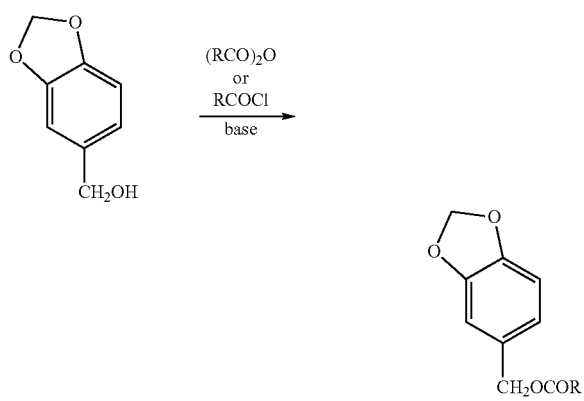

The piperonyl alcohol produced in Synthesis Example 1 was reacted with a carboxylic acid anhydride or a carboxylic acid chloride in the presence of a base. The reaction mixture was purified with distilled water or by silica gel column chromatography to produce piperonyl esters having different substituents $R_2$.

COMPARATIVE SYNTHESIS EXAMPLE 3

Synthesis of piperonyl amines

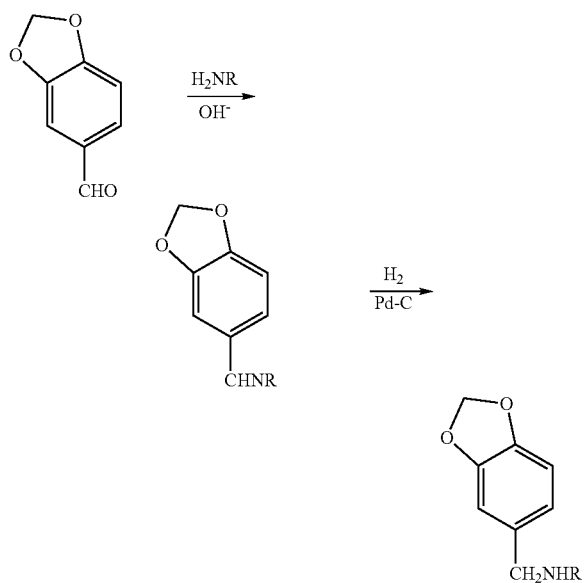

A Schiff base obtained from heliotropin and an alkyl amine was hydrogenated in the presence of 5% Pd—C to produce piperonyl amines having different substituents $R_3$.

EXAMPLE 1

Melanogenesis Inhibition Test and Cytotoxicity Test

The following tests a) and b) were conducted on the compounds shown in Synthesis Examples and Comparative Synthesis Examples to examine their melanogenesis-inhibiting effects.

a) Cytotoxicity test (using B16 melonoma cells)

b) Melanogenesis inhibition test (visual evaluation) (using B16 melonoma cells)

Evaluation Methods $8 \times 10^4$ B16 melanoma cells were inoculated in a plastic-made culture flask (25 cm$^2$). The cells were cultured in a 10% serum-containing DMEN medium (produced by Nissui Pharmaceutical co., Ltd., trade name) in the presence of 5% carbon dioxide at 37° C. 3 days later, a test sample diluted with ethanol was added thereto, and culture was conducted for 3 days. After the completion of the culture, the medium was removed and the flask contents were washed with a phosphate buffer solution (hereinafter referred t as PBS). The cells were peeled from the flask inner wall using a medium containing trypsin and EDTA (ethylenediaminetetraacetic acid). The resulting cells suspension was centrifuged to recover cells. Part of the cells was taken and the number of cells was measured using a Coulter counter. The concentration at which the number of cells became 95 to 100 (when the number of cells in the case of using test sample-free ethanol (solvent) was taken as 100) was taken as a concentration giving no cytotoxicity. A melanogenesis inhibition test was carried out in this concentration range. The cells obtained were washed once with PBS and then the whiteness of the precipitate was rated visually based on the following evaluation standard.

Evaluation Standard

−: Same as the solvent control (black)

+−: Slightly different from the solvent control (black-gray)

+: Clearly different from the solvent control (gray)

++: Coloring of cells is very low (gray-white)

+++: No coloring of cells (white)

The results are shown in Tables 2, 3, 4 and 5.

TABLE 2

| | Synthesis Example | R = | Concentration (μg/ml) | | |
|---|---|---|---|---|---|
| | | | 12.5 | 6.3 | 3.1 |
| Example | 5 | Propyl | + | N.T. | N.T. |
| | 2 | Butyl | ++ | N.T. | N.T. |
| | 6 | Isobutyl | ++ | N.T. | N.T. |
| | 7 | Isoamyl | ++ | N.T. | N.T. |
| | 8 | Hexyl | ++ | N.T. | N.T. |
| | 9 | Octyl | + | + | N.T. |
| | 10 | 1-Mentyl | +++ | ++ | + |
| Comparative Example | 3 | Methyl | − | N.T. | N.T. |
| | 4 | Ethyl | − | N.T. | N.T. |

N.T.: not tested

As is clear from Table 2, the compounds whose R is 3 or more carbon atoms, showed an effect and 1-menthyl ether showed a particularly superior fair skin effect.

TABLE 3

| | Synthesis Example | $R_2$ = | Concentration (μg/ml) 12.5 |
|---|---|---|---|
| Comparative Example (piperonyl ester) | Comparative Example 2 | Butyl | — |
| | Comparative Example 2 | Hexyl | — |
| | Comparative Example 2 | Octyl | — |
| | Comparative Example 2 | Dodecyl | — |

TABLE 4

|  | Synthesis Example | $R_3$ = | Concentration (μg/ml) 12.5 |
|---|---|---|---|
| Comparative Example (piperonyl amine) | Comparative Example 3 | Butyl | — |
| | Comparative Example 3 | Hexyl | — |
| | Comparative Example 3 | Octyl | — |
| | Comparative Example 3 | Dodecyl | — |

As is clear from Table 3 and Table 4, the piperonyl amines and the piperonyl esters showed no melanogenesis hindrance effect and it was confirmed that melanogenesis inhibition is an effect unique to the compound of the present invention.

TABLE 5

|  | X | Y | $R_1$ | Concentration (μg/ml) 12.5 |
|---|---|---|---|---|
| Synthesis Example 2 | X, Y = OCH$_2$O | | Butyl | ++ |
| Comparative Synthesis Example 1 | OH | OMe | Methyl | − |
| Comparative Synthesis Example 1 | OH | OEt | Methyl | − |
| Comparative Synthesis Example 1 | OH | OEt | Ethyl | − |
| Comparative Synthesis Example 1 | OH | OEt | Butyl | +− |
| Comparative Synthesis Example 1 | OH | OMe | Butyl | +− |
| Comparative Synthesis Example 1 | OMe | OMe | Butyl | − |

As is clear from Table 5, the melanogenesis inhibitor of the present invention containing the piperonyl alcohol having a methylendioxy group as an aromatic ring substituent showed the highest melanogensis hindrace effect.

EXAMPLE 2

Mechanism for Melanogenesis Hindrance

A tyrosinase activity hindrance test and a tyrosinase biosynthesis hindrance test were conducted according to the following test methods to examine the mechanism for hindrance of melanin denovo synthesis. Kojic acid hitherto used widely as a fair skin preparation was used as a control.

Test Method for Tyrosinase Activity Hindrance

100 μl of a suspension containing 5×10$^5$/ml of B16 melanoma cells was inoculated into a 96-well plate, and culture was made at 37° C. overnight in 5% CO$_2$. Next day, the culture medium was removed and 90 μl of 1% Triton X100 was added. The resulting mixture was allowed to stand at room temperature for 1 hour. Then, the plate was shaken gently, after which there were added 90 μl of 1% DOPA and 20 μl of a sample diluted with ethanol to a given concentration. Immediately, measurement was made at 450 nm and the value obtained was taken as a measured value of 0 hour. Thereafter, the plate was transferred into a 37° C. incubator to give rise to a reaction for 1 to 3 hours. During the period, measurement was made at intervals of 1 hour. The activity hindrance effect of the sample was determined as a proportion to the melanin amount when no sample was added.

Test Method for Tyrosinase Biosynthesis Hindrance

In this method, tyrosinase biosynthesis hindrance is indicated indirectly by measuring intra-cell tyrosinase activity. 100 μl of a suspension containing 3×10$^5$/ml of B16 melanoma cells was inoculated into a 96-well plate, and culture was made at 37° C. overnight in 5% CO$_2$. Next day, the medium was changed with 200 μl of a sample-containing culture medium, and culture was made for 2 days under the same conditions. Thereafter, the supernatant liquid was removed and the residue was washed with 200 μl of a phosphate buffer solution twice. Then, 100 μl of 1% Triton X100 was added and the mixture was allowed to stand at room temperature for 1 hour, followed by gentle shaking. Next, 100 μl of 1% DOPA was added. Measurement was made in the same manner as in the above test method for tyrosinase activity hindrance. Incidentally, in this test, two same plates were prepared and one of them was used for measurement by MTT method in order to prove that there was no cytotoxicity.

The results are shown in Tables 6 to 8.

TABLE 6

Tyrosinase biosynthesis hindrance of piperonyl 1-menthyl ether

| Concentration | Hindrance % | Cell propagation rate % |
|---|---|---|
| 12.5 ppm | 80.0 | 91.0 |
| 6.3 ppm | 63.0 | 98.8 |
| 3.1 ppm | 48.0 | 104.7 |

TABLE 7

Tyrosinase activity hindrance of kojic acid

| Concentration | Hindrance % |
|---|---|
| 200 ppm | 59.8 |
| 100 ppm | 33.0 |
| 50 ppm | 21.4 |

TABLE 8

Tyrosinase biosynthesis hindrance of kojic acid

| Concentration | Hindrance % | Cell propagation rate % |
|---|---|---|
| 200 ppm | 21.0 | 96.2 |
| 100 ppm | 21.0 | 97.3 |
| 50 ppm | 21.0 | 100.8 |

As is clear from Table 6, piperonyl 1-menthyl ether exhibited a tyrosinase biosynthesis hindrance effect concentration-dependently at concentrations of no cytotoxicity. Incidentally, there was no tyrosinase activity hindrance effect. Meanwhile, as is clear from Tables 7 and 8, kojic acid hindered tyrosinase activity concentration-dependently. From this result, it was confirmed that the melanogenesis inhibitor of the present invention does not hinder tyrosinase activity, but hinders tyrosinase biosynthesis and shows a novel melanogenesis-hindering activity and that this activity is 10 times or more the activity of kojic acid.

EXAMPLE 3

Safety Test

On piperonyl 1-menthyl ether were carried out a skin sensitization test, a skin irritation test and a phototoxicity test to examine the safety of the compound. The results are shown in Table 9.

TABLE 9

| Safety test of piperonyl 1-menthyl ether | |
|---|---|
| skin irritation | Negative (1%, open coating to guinea pig) |
| skin sensitization | Negative (1%, guinea pig maximization) |
| Phototoxicity | Negative (1%, UV application to guinea pig) |

In all tests, the results were negative at a concentration of 1%, and it was confirmed that the melanogenesis inhibitor of the present invention is highly safe.

EXAMPLE 4

A cream having the following composition was produced by an ordinary method.

| | |
|---|---|
| Stearic acid | 6.0% by mass |
| Sorbitan monostearate | 2.0% by mass |
| Polyoxyethylene (20 moles) sorbitan mono-stearate | 1.5% by mass |
| Propylene glycol | 10.0% by mass |
| Piperonyl 1-menthyl ether | 7.0% by mass |
| Glycerine trioctanoate | 10.0% by mass |
| Squalene | 5.0% by mass |
| Sodium hydrogensulfite | 0.01% by mass |
| Ethylparaben | 0.3% by mass |
| Perfume | Appropriate |
| Deionized water | Residue |

EXAMPLE 5

A cream having the following composition was produced by an ordinary method.

| | |
|---|---|
| Stearyl alcohol | 7.0% by mass |
| Stearic acid | 2.0% by mass |
| Hydrogenated lanolin | 2.0% by mass |
| Squalane | 5.0% by mass |
| 2-Octyldodecyl alcohol | 6.0% by mass |
| Polyoxyethylene (25 moles) cetyl alcohol ether | 3.0% by mass |
| Glycerine mono-stearate | 2.0% by mass |
| Propylene glycol | 5.0% by mass |
| Piperonyl 1-menthyl ether | 0.05% by mass |
| Perfume | Appropriate |
| Sodium hydrogensulfite | 0.03% by mass |
| Ethylparaben | 0.3% by mass |
| Deionized water | Residue |

EXAMPLE 6

An emulsion having the following composition was produced by an ordinary method.

| | |
|---|---|
| Stearic acid | 2.5% by mass |
| Cetyl alcohol | 1.5% by mass |
| Vaseline | 5.0% by mass |
| Liquid paraffin | 10.0% by mass |
| Polyoxyethylene (10 moles) mono-oleic acid ester | 2.0% by mass |
| Polyethylene glycol 15 | 3.0% by mass |
| Triethanolamine | 1.0% by mass |
| Piperonyl 1-menthyl ether | 10.0% by mass |
| Sodium hydrogensulfite | 0.01% by mass |
| Ethylparaben | 0.3% by mass |
| Carboxyvinyl polymer | 0.05% by mass |
| Perfume | Appropriate |
| Deionized water | Residue |

EXAMPLE 7

An emulsion having the following composition was produced by an ordinary method.

| (Oil phase) | |
|---|---|
| Stearyl alcohol | 1.5% by mass |
| Squalene | 2.0% by mass |
| Vaseline | 2.5% by mass |
| Deodorized liquid lanolin | 1.5% by mass |
| Oenothera tetraptera Cav. oil | 2.0% by mass |
| Isopropyl myristate | 5.0% by mass |
| Glycerine mono-oleate | 2.0% by mass |
| Polyoxyethylene (60 moles) hardened castor oil | 2.0% by mass |
| Tocopherol acetate | 0.05% by mass |
| Ethylparaben | 0.2% by mass |
| Butylparaben | 0.1% by mass |
| Piperonyl 1-menthyl ether | 1.0% by mass |
| Arbutin | 1.0% by mass |
| Perfume | Appropriate |
| (Aqueous phase) | |
| Sodium hydrogensulfite | 0.01% by mass |
| Glycerine | 5.0% by mass |
| Sodium hyaluronate | 0.01% by mass |
| Carboxyvinyl polymer | 0.2% by mass |
| Potassium hydroxide | 0.2% by mass |
| Purified water | Residue |

EXAMPLE 8

A jelly having the following composition was produced by an ordinary method.

| | |
|---|---|
| 95% ethyl alcohol | 10.0% by mass |
| Dipropylene glycol | 15.0% by mass |
| Polyoxyethylene (50 moles) oleyl alcohol ether | 2.0% by mass |
| Carboxyvinyl polymer | 1.0% by mass |
| Sodium hydroxide | 0.15% by mass |
| L-alginine | 0.1% by mass |
| Piperonyl 1-menthyl ether | 1.0% by mass |
| Piperonyl n-butyl ether | 1.0% by mass |
| Methylparaben | 0.2% by mass |
| Perfume | Appropriate |
| Deionized water | Residue |

EXAMPLE 9

A beauty lotion having the following composition was produced by an ordinary method.

| | |
|---|---|
| Ethanol (95%) | 10.0% by mass |
| Polyoxyethylene (20 moles) octyldodecanol | 1.0% by mass |
| Methylparaben | 0.15% by mass |
| Pantothenol ethyl ether | 0.1% by mass |
| Piperonyl isoamyl ether | 0.05% by mass |
| Potassium hydroxide | 0.1% by mass |
| Glycerine | 5.0% by mass |
| Dipropylene glycol | 10.0% by mass |
| Sodium hydrogensulfite | 0.03% by mass |
| Carboxyvinyl polymer | 0.2% by mass |
| Purified water | Residue |

EXAMPLE 10

A pack having the following composition was produced by an ordinary method.

| | |
|---|---|
| Dipropylene glycol | 5.0% by mass |
| Polyoxyethylene (60 moles) hardened castor oil | 5.0% by mass |
| Piperonyl lauryl ether | 0.1% by mass |
| Piperonyl 1-menthyl ether | 0.1% by mass |
| Olive oil | 5.0% by mass |
| Tocopherol acetate | 0.2% by mass |
| Ethylparaben | 0.2% by mass |
| Perfume | 0.2% by mass |
| Sodium hydrogensulfite | 0.03% by mass |
| Polyvinyl alcohol (saponification degree: 90, polymerization degree: 2000) | 13.0% by mass |
| Ethanol | 7.0% by mass |
| Purified water | Residue |

EXAMPLE 11

An ointment having the following composition was produced by an ordinary method.

| | |
|---|---|
| Polyoxyethylene (30 moles) cetyl ether | 2.0% by mass |
| Glycerine mono-stearate | 10.0% by mass |
| Liquid paraffin | 10.0% by mass |
| Vaseline | 40.0% by mass |
| Cetanol | 6.0% by mass |
| Methylparaben | 0.1% by mass |
| Butylparaben | 0.1% by mass |
| Glycerine mono-stearate | 2.0% by mass |
| Piperonyl 1-menthyl ether | 2.0% by mass |
| Propylene glycol | 10.0% by mass |

-continued

| | |
|---|---|
| Deionized water | Residue |
| Perfume | Appropriate |

(Production)

Propylene glycol is added to deionized water, followed by heating to obtain a solution. The solution is kept at 70° C. (this becomes an aqueous phase). Other components are mixed at 70° C. to obtain a solution (this becomes an oil phase). The oil phase is added to the aqueous phase; the mixture is uniformly emulsified using a homomixer; the emulsion is cooled and then packed to obtain a product.

According to the present invention there are provided a novel melanogenesis inhibitor which contains a piperonyl alcohol derivative and which has an excellent melanogenesis-inhibiting effect; and a skin preparation which contains the novel melanogenesis inhibitor and which is highly stable and highly safe and has an excellent fair skin effect.

According to the present invention there is also provided a novel piperonyl alcohol derivative which is included in the above-mentioned piperonyl alcohol derivative and which is useful as a component of the above novel melanogenesis inhibitor.

The invention claimed is:

1. A melanogenesis inhibitor represented by the following formula:

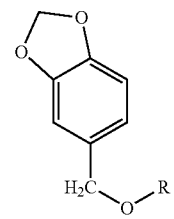

wherein R is an alicyclic alkyl group derived from a cyclic monoterpene alcohol.

2. A skin preparation characterized by containing a melanogenesis inhibitor of the formula set forth in claim 1.

3. A skin preparation characterized by containing 0.001 to 20.0% by mass of a melanogenesis inhibitor set forth in claim 1.

4. A skin preparation according to claim 2, which has a form of cream, lotion, emulsion, jelly, beauty lotion, pack or ointment.

5. A skin preparation according to claim 3, which has a form of cream, lotion, emulsion, jelly, beauty lotion, pack or ointment.

* * * * *